US00PP28677P3

(12) United States Plant Patent
Suphachadiwong

(10) Patent No.: US PP28,677 P3
(45) Date of Patent: Nov. 21, 2017

(54) ***VANDA* PLANT NAMED 'SPCDW1510'**

(50) Latin Name: ***Vanda Jones* ex R. Br.**
Varietal Denomination: SPCDW1510

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 5 days.

(21) Appl. No.: 14/999,832

(22) Filed: Jul. 6, 2016

(65) Prior Publication Data

US 2017/0013763 P1 Jan. 12, 2017

(30) Foreign Application Priority Data

Jul. 8, 2015 (QZ) ..... PBR 2015/1574

(51) Int. Cl.
*A01H 5/02* (2006.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen Redden
(74) *Attorney, Agent, or Firm* — Samuel R. McCoy Jr.

(57) ABSTRACT

A new and distinct *Vanda* cultivar named 'SPCDW1510' which is characterized by pink sepals and petals which are margined red-purple and heavily dotted and blotched red-purple, sepals that also exhibit a dark red-purple irregular tessellation pattern, a labellum with purple lateral lobes that are striped red-purple and a dark red-purple central lobe, and the stability of these characteristics from generation to generation.

3 Drawing Sheets

Latin name of the genus and species: The Latin name of the genus and species of the novel variety disclosed herein is *Vanda* Jones ex R. Br.

Variety denomination: The inventive variety of *Vanda* disclosed herein has been given the variety denomination 'SPCDW1510'.

CROSS REFERENCE TO RELATED APPLICATIONS

This application claims priority to the Community Plant Variety Rights application number 2015/1574, filed Jul. 8, 2015, which is herein incorporated by reference.

BACKGROUND OF THE INVENTION

Parentage: The *Vanda* variety 'SPCDW1510' is the result of a planned breeding program. The new variety originated as a seedling from the crossing of an unnamed *Vanda* seed parent (not patented) with an unnamed *Vanda* pollen parent (not patented). Both parents were developed by, and are owned by, the inventor and were never commercially released. The crossing was made by the inventor in his research greenhouse in Bangphra, Thailand in December of 2005.

The new variety was first selected in November of 2009, in a research greenhouse in Bangphra, Thailand belonging to the inventor. After identifying the new variety as a potentially interesting selection, the inventor continued confidential testing and propagation of 'SPCDW1510', assessing stability of the unique characteristics of this variety.

Asexual Reproduction: Asexual reproduction of the new cultivar 'SPCDW1510', by way of mericloning, was first initiated in May of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1510' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1510'. These characteristics in combination distinguish 'SPCDW1510' as a new and distinct *Vanda* cultivar:

1. *Vanda* 'SPCDW1510' exhibits sepals and petals which are pink and margined red-purple; and
2. *Vanda* 'SPCDW1510' exhibits sepals and petals which are heavily dotted and blotched red-purple; and
3. *Vanda* 'SPCDW1510' exhibits sepals with a prominent red-purple irregular tessellation pattern; and
4. *Vanda* 'SPCDW1510' exhibits a labellum with purple lateral lobes which are striped red-purple, and a dark red-purple central lobe.

BOTANICAL DESCRIPTION OF THE PLANT

Figure 1:
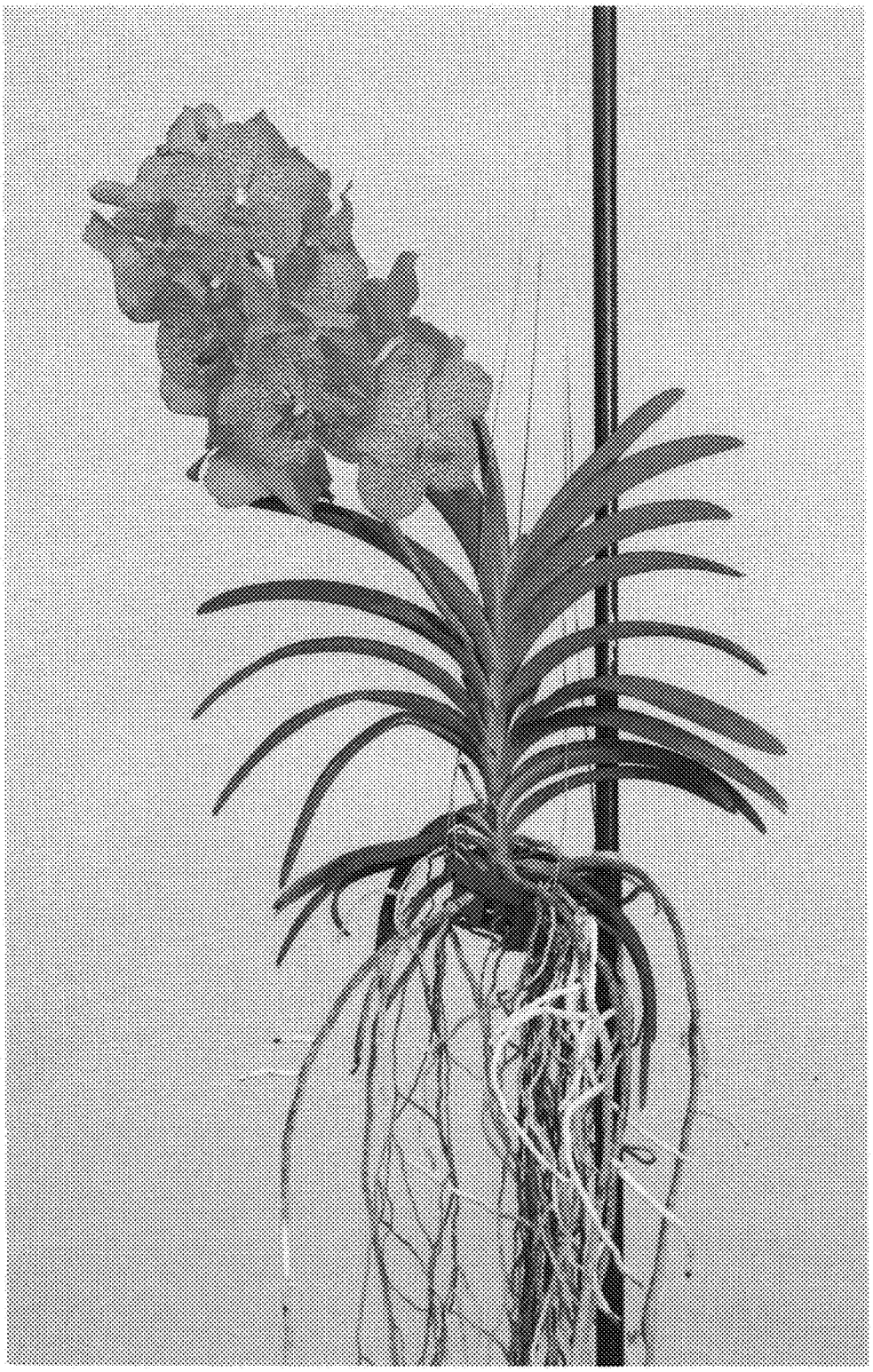
FIG. 1 illustrates, as nearly true as it is reasonably possible to make the same in color photographs of this type, an exemplary plant of 'SPCDW1510' grown in a commercial greenhouse in Honselersdijk, the Netherlands. This plant is approximately 6 years old from the time of mericloning, shown planted in an 8 by 8 cm container.
Figure 2:
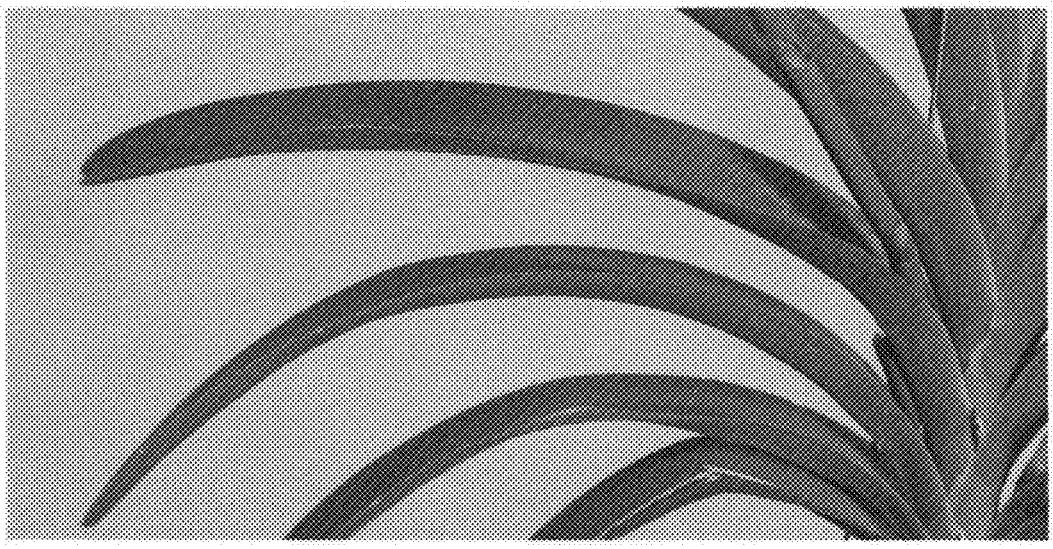
FIG. 2 illustrates, as nearly true as it is reasonably possible to make the same in color photographs of this type, the typical foliage of 'SPCDW1510'.
Figure 3:
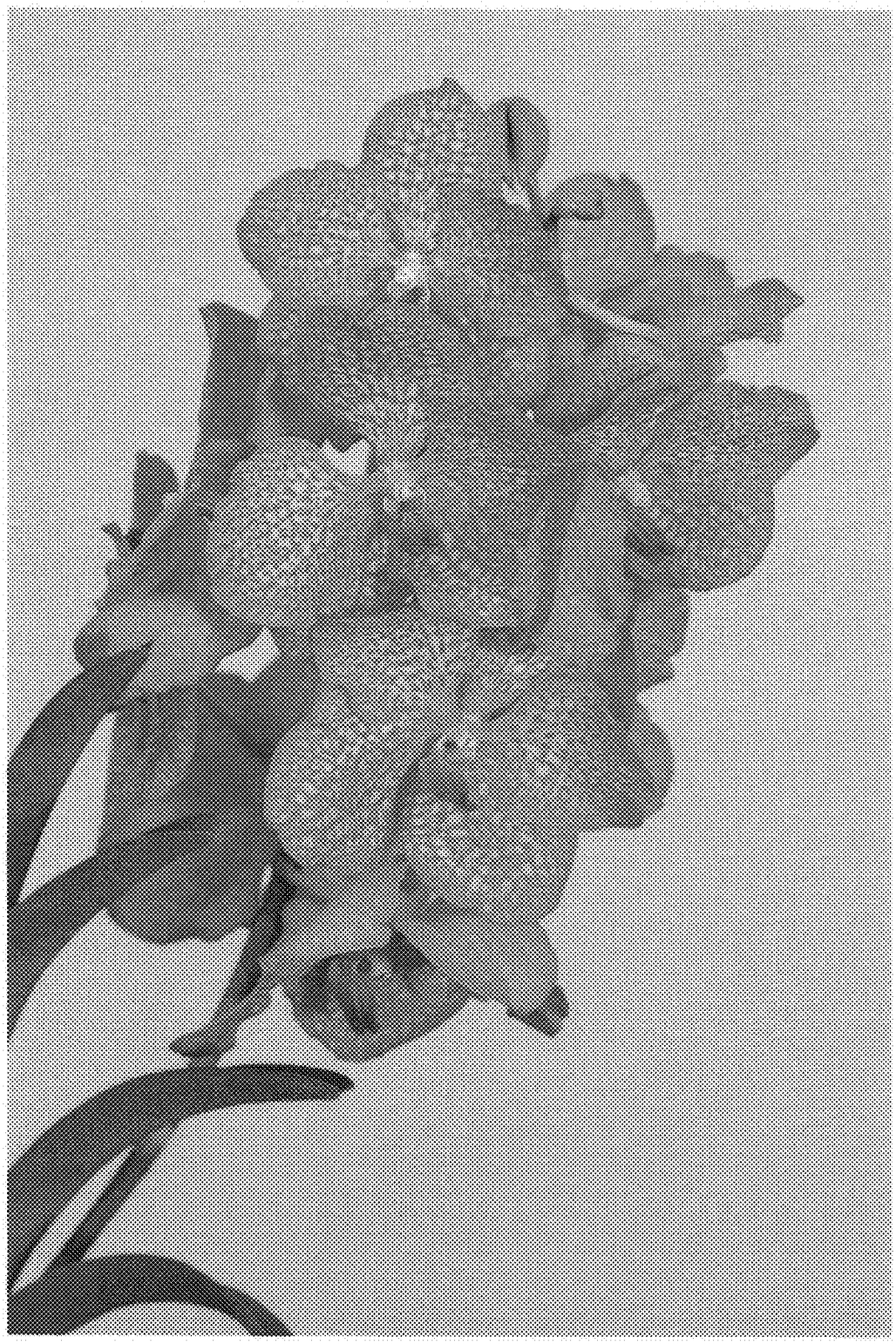
FIG. 3 illustrates, as nearly true as it is reasonably possible to make the same in color photographs of this type, the typical inflorescence and flower of 'SPCDW1510'.

The following observations and measurements made in June of 2016 describe averages from a sample set of six specimens of six year-old 'SPCDW1510' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1510' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1510' and comparisons with other varieties of *Vanda* are provided below.

Plant description:

- *Growth habit.*—Perennial; monopodial, upright. Single monopodial leafy stem, with flowers carried slightly above the leaf plane with inflorescences growing from the leaf axils.
- *Average height from base (plant grown in hanging basket, so no soil line present) to foliar plane.*—38.7 cm.
- *Average height from base (plant grown in hanging basket, so no soil line present) to top of floral plane.*—50.2 cm.
- *Plant spread.*—Average of 45.6 cm.
- *Appropriate container size.*—8 cm by 8 cm rectangular hanging basket.
- *Growth rate.*—Moderate.
- *Plant vigor.*—Moderate.
- *Propagation type.*—Tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Similar to other *Vanda* varieties.
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Densely rooting; with aerial roots only.
- *Dimensions, mature roots.*—68.5 cm long with a diameter of 0.5 cm, on average.
- *Texture.*—Very fleshy; non-fibrous.
- *Color.*—Greyed-Green, near RHS 192A to 192C; root apex is yellow-green, RHS 146A.

Stem:

- *Branching habit.*—Monopodial; no lateral branches present.
- *Number of primary (main) stems per plant.*—One.
- *Number of secondary (lateral) branches per plant.*—None.
- *Appearance and shape.*—Circular, formed by the leaf sheaths.
- *Length.*—19.0 cm.
- *Diameter.*—1.1 cm.
- *Internode length.*—0.9 cm.
- *Luster.*—Matte.
- *Aspect.*—Near vertical.
- *Strength.*—Very strong.
- *Color, juvenile.*—Yellow-green, near RHS 145D.
- *Color, mature.*—Yellow-green, near RHS 145D.
- *Color at internodes.*—Yellow-green, near RHS 145D.
- *Pubescence.*—Glabrous.

Foliage:

- *Arrangement.*—Distichous.
- *Quantity.*—Approximately 30 leaves per plant.
- *Dimensions.*—21.3 cm long and 2.1 cm wide, on average.
- *Shape of blade.*—Ligulate; strongly carinate.
- *Aspect.*—Moderately curved.
- *Apex.*—Unequal praemorse.
- *Base.*—Sheathing.
- *Sheath dimensions.*—3.4 cm long and 1.5 cm wide, on average.
- *Sheath color.*—Yellow-green, near RHS 150B to 150C.
- *Margin.*—Entire.
- *Pubescence, texture and luster of adaxial surface.*—Glabrous, smooth, and very slightly glossy.
- *Pubescence, texture and luster of abaxial surface.*—Glabrous, smooth, and matte.
- *Color.*—Juvenile foliage, adaxial surface — Green, near RHS 143A. Juvenile foliage, abaxial surface — Green, near RHS 143A. Mature foliage, adaxial surface — Green, near RHS 137B. Mature foliage, abaxial surface — In between green, RHS 143A, and yellow-green, RHS 144A.
- *Venation.*—Parallel.
- *Venation color, adaxial surface.*—Green, near RHS NN137B.
- *Venation color, abaxial surface.*—Yellow-green, RHS 144A.
- *Petiole.*—No petioles present; leaves sessile.

Inflorescence:

- *Inflorescence arrangement.*—Axially placed raceme.
- *Natural flowering season.*—Autumn into winter.
- *Time to flower.*—Approximately 10 months.
- *Flowers per inflorescence.*—Average of 17; 16 open flowers and 1 buds.

*Inflorescence height.*—Approximately 28.5 cm (measured from base of lowest flower to top of upper flower).

*Inflorescence diameter.*—Approximately 20.4 cm.

*Peduncle.*—Dimensions — Approximately 40.8 cm long and 0.7 cm wide. Aspect — Generally at a 35 degree angle to lateral branch axis. Strength — Moderately strong. Texture and luster — Glabrous and moderately glossy. Color — Yellow-green, RHS 144A.

Bud:

*Length.*—Average of 1.6 cm.

*Diameter.*—Average horizontal diameter is 1.4 cm; the vertical diameter is 2.0 cm.

*Shape.*—Cubic, with a deltoid apex which is pointed downward.

*Pubescence, texture and luster.*—Glabrous, smooth and slightly glossy.

*Color.*—In between red-purple, near RHS 70A, and purple, near N77B; the base is tinged yellow-green, near RHS 150C.

Flower:

*Flower type.*—Zygomorphic (orchidaceous), typical shape for the genus *Vanda*.

*Flowering habit.*—Moderate.

*Shape.*—Zygomorphic, single; consisting of three sepals and three petals, one of which is transformed into a labellum.

*Aspect.*—Flowers are outward-facing to slightly nodding.

*Vertical height.*—Approximately 11.3 cm.

*Diameter.*—Approximately 10.6 cm.

*Depth.*—Approximately 3.7 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 5.5 cm. Width — Approximately 5.2 cm. Shape — Broad ovate to near orbicular. Apex — Undeeply retuse to obtuse. Base — Cuneate. Margin — Entire; moderately undulated. Pubescence, texture and luster of upper surface — Glabrous, velvety and matte. Pubescence, texture and luster of lower surface — Glabrous, velvety and matte. Color when opening, upper surface — Purple-violet, near RHS N80D yet lighter, and margined purple, near RHS NN78C to NN78D; heavily dotted and blotched red-purple, near RHS N74A, and purple, near RHS NN78A and NN78B. Color when opening, lower surface — Purple-violet, near RHS N80B to N80C, and fading to violet towards the base, near RHS 84C. Color when fully opened, upper surface — Purple, near RHS N78D, and margined darker, near RHS NN78C to NN78D; heavily dotted and blotched red-purple, near RHS N74A, and purple, near RHS NN78A. Color when fully opened, lower surface — Purple-violet, near RHS N80C to N80D, and margined purple, near RHS N78C to N78D. Fading, upper surface — Not fading. Fading, lower surface — Not fading. Venation — Densely reticulate. Venation color, fully opened, upper surface — Purple, near RHS N78D, and margined darker, near RHS NN78C to NN78D; heavily dotted and blotched red-purple, near RHS N74A, and purple, near RHS NN78A. Venation color, fully opened, lower surface — Purple, near RHS NN78B.

*Labellum.*—Shape — Three-lobed, lateral lobes are involute and the central lobe is revolute. Length — Central lobe — Approximately 2.3 cm. Lateral lobes — Approximately 0.8 cm. Width — Central lobe — Approximately 1.2 cm. Lateral lobes — Approximately 0.7 cm. Apex, central lobe — Strongly emarginate. Apex, lateral lobes — Emarginate. Base, central and lateral lobes — Cuneate. Margin, central lobe — Irregular; slightly undulated. Margin, lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte; apex is glossy. Lateral lobes — Glabrous, velvety, and matte. Color when opening, upper surface — Central lobe — Red-purple, near RHS 72A; apex is red-purple, near RHS 71A, and darker. Lateral lobes — Purple, near RHS 75D; striped pink, near RHS NN74B, and fading to pink at the base, near RHS NN74C. Color when opening, lower surface — Central lobe — Purple, near RHS 75A to 75B, and margined red-purple, near RHS N74A; apex is red-purple, near RHS 71A, and darker. Lateral lobes — Purple, near RHS 75C to 75D; margins are tinged darker, near RHS 75A. Color when fully opened, upper surface — Central lobe — Red-purple, in between near RHS 71A and N74A; fading lighter toward the base, near RHS N74B; apex is red-purple, near RHS 71A, yet considerably darker. Lateral lobes — Purple, RHS 75C, and striped red-purple, near RHS 72C, with a yellow dot at the base, near RHS 22A to 22B. Color when fully opened, lower surface — Central lobe — Pink, near RHS NN74D; middle section is darker, near RHS NN74B; apex is red-purple, near RHS 71A, yet darker. Lateral lobes — Purple, near RHS 75A to 75B. Fading, upper surface — Not fading. Fading, lower surface — Not fading. Venation — Densely reticulate. Venation color, fully opened, upper surface — Central lobe — Red-purple, in between near RHS 71A and N74A, and fading lighter towards the base, near RHS N74B; apex is darker, near RHS 71A yet considerably darker. Lateral lobes — Purple, RHS 75C, and striped red-purple, near RHS 72C, with a yellow-orange dot at the base, near RHS 22A to 22B. Venation color, fully opened, lower surface — Central lobe — Pink, near RHS NN74D; middle section is darker, near RHS NN74B; apex is red-purple, near RHS 71A, yet darker. Lateral lobes — Purple, near RHS 75A to 75B.

*Callosities.*—Dimensions — 1.3 cm long and 0.8 cm wide, on average. Color — Red-purple, in between near RHS 71A and N74A.

*Spurs.*—Quantity — Average of 1. Length — Approximately 0.7 cm. Diameter — Approximately 0.3 cm. Vertical height — Approximately 0.6 cm, at the base. Shape — Short triangular. Apex — Bluntly acute. Base — Broad Cuneate. Pubescence, texture and luster — Glabrous, smooth, and matte. Color — Purple, near RHS 75D.

*Sepals.*—Quantity — Average of 3 unfused sepals. Arrangement — One dorsal sepal and two lateral sepals. Length — Dorsal sepal — Approximately 5.9 cm. Lateral sepals — Approximately 6.2 cm. Width — Dorsal sepal — Approximately 4.9 cm. Lateral sepals — Approximately 6.1 cm. Shape — Dorsal sepal — Broad ovate. Lateral sepals — Broad ovate. Apex, dorsal and lateral sepals — Obtuse. Base, dorsal and lateral sepals — Cuneate. Margin, dorsal and lateral sepals — Entire; dorsal sepal is slightly undulated and lateral sepals are moderately undulated. Pubescence, texture and luster — Glabrous, velvety, and matte on both the upper and lower sepal surfaces. Color when opening, upper surface — Dorsal sepal — White, near RHS NN155B, and margined purple, near RHS N78D; sepals are heavily dotted pink, RHS NN74A to NN74B. Lateral sepals — White, near RHS NN155B, and margined purple, near RHS N78D; sepals are heavily dotted pink, RHS NN74A to NN74B. Color when opening, lower surface — Dorsal sepal — Purple-violet, near RHS N80B to N80C, and fading to violet towards the base, RHS 84C. Lateral sepals — Purple-violet, near RHS N80B to N80C, and fading to violet towards the base, RHS 84C. Color when fully opened, upper surface — Dorsal sepal — In between red-purple, near RHS N74D, and purple, near RHS 77D, and margined purple, near RHS NN78C to NN78D; sepals are heavily dotted and blotched darker, near RHS N78A to N78B. Lateral sepals — In between red-purple, near RHS N74D, and purple, near RHS 77D, and margined purple, near RHS NN78C to NN78D. Color when fully opened, lower surface — Dorsal sepal — Purple, near RHS N80D yet lighter, and margined darker, near RHS N78B and NN78C. Lateral sepals — Purple, near RHS N80D yet lighter, and margined darker, near RHS N78B and NN78C. Fading, upper surface — Not fading. Fading, lower surface — Not fading. Venation — Densely reticulate. Venation color, fully opened, upper surface — Dorsal sepal — In between red-purple, near RHS N74D, and purple, near RHS 77D, and margined purple, near RHS NN78C to NN78D; sepals are heavily dotted and blotched darker, near RHS N78A to N78B. Lateral sepals — Purple, near RHS NN78A and NN78B. Venation color, fully opened, lower surface — Dorsal sepal — Purple, near RHS NN78B to NN78C. Lateral sepals — Purple, near RHS NN78B to NN78C.

*Pedicels.*—Length — Approximately 6.5 cm. Diameter — Approximately 0.4 cm. Angle — Approximately 70 degree angle to peduncle axis. Strength — Moderate. Texture — Glabrous, axially angled with 5 "ribs", axially twisted (due to resupination). Luster — Glossy. Color — Purple, RHS 77B to 77C, and tinged greyed-red towards the proximal end, near RHS 182C.

*Bract.*—Quantity — One bract present at the base of each pedicel. Shape — Ovate; folded around the base of each pedicel. Dimensions — Average of 1.7 cm long and 1.5 cm wide. Apex — Broad acute. Base — Broad cuneate. Margins — Entire. Color, both surfaces — Yellow-green, near RHS N144D.

Reproductive organs:

*Column.*—Length — Approximately 0.7 cm. Diameter — Approximately 0.6 cm. Color — Pink, RHS NN74C, and fading to a lighter purple on the underside, RHS 75B.

*Ovary.*—Position — Inferior. Diameter — Approximately 0.6 cm. Color — Yellow-green, RHS 150C.

*Pollinia color.*—Yellow-orange, RHS 15A.

Seed and fruit: No fruit and seed production has been detected to date.

Comparison With the Parent Plants

Plants of the new cultivar 'SPCDW1510' differ from the unnamed *Vanda* seed parent (not patented) by the characteristics described in Chart 1.

CHART 1

| Characteristic | 'SPCDW1510' | Unnamed seed parent |
|---|---|---|
| Flower color. | Background color is a lighter pink. | Background color is a darker pink. |
| Flower color pattern. | Higher degree of tessellation. | Less tessellation. |
| Inflorescence. | Racemes are longer than those of the seed parent. | Racemes are shorter than those of 'SPCDW1510'. |
| Flower size. | Smaller flowers than seed parent. | Larger flowers than 'SPCDW1510'. |
| Plant size. | More compact than the seed parent. | Larger than 'SPCDW1510'. |
| Length of foliage. | Leaves are shorter than those of seed parent. | Leaves are longer than those of 'SPCDW1510'. |
| Plant vigor. | More vigorous; faster growing and quicker to flower when compared to the seed parent. | Less vigorous; slower growing and slower to flower than 'SPCDW1510'. |

Plants of the new cultivar 'SPCDW1510' differ from the unnamed *Vanda* pollen parent (not patented) by the characteristics described in Chart 2.

CHART 2

| Characteristic | 'SPCDW1510' | Unnamed pollen parent |
|---|---|---|
| Flower color. | Background color is a darker pink. | Background color is a lighter pink. |
| Color pattern on the petals and sepals. | More densely dotted and blurred. | Fewer dots and blurs. |
| Inflorescence. | Racemes are shorter than those of the pollen parent. | Racemes are longer than those of 'SPCDW1510'. |
| Flower size. | Larger flowers than pollen parent. | Smaller flowers than 'SPCDW1510'. |
| Plant size. | Larger than the pollen parent. | Smaller than 'SPCDW1510'. |
| Plant vigor. | Slower growing than the pollen parent. | Faster growing than 'SPCDW1510'. |

Comparison With the Most Similar *Vanda* Cultivar Known to the Inventor

Plants of the new cultivar 'SPCDW1510' are most similar to the cultivar, *Vanda* 'SPCDW1309' (not patented). A comparison of 'SPCDW1510' with *Vanda* 'SPCDW1309' is described in Chart 3.

CHART 3

| Characteristic | 'SPCDW1510' | 'SPCDW1309' |
|---|---|---|
| Sepal Arrangement. | Lesser degree of sepal overlap compared to 'SPCDW1309'. | Higher degree of sepal overlap compared to 'SPCDW1510'. |
| Petal shape. | Less broad than 'SPCDW1309'. | More broad than 'SPCDW1510'. |
| Flower color. | Background color is much darker pink. | Background color is much lighter pink. |
| Patterning on the lateral sepals. | Appears more as a tessellation pattern. | Appears more as irregular blurs. |

CHART 3-continued

| Characteristic | 'SPCDW1510' | 'SPCDW1309' |
|---|---|---|
| Color of petal and sepal pattern. | Pinkish purple color is brighter. | Pinkish purple color is duller. |

That which is claimed is:

1. A new and distinct variety of *Vanda* plant named 'SPCDW1510', substantially as described and illustrated herein.

* * * * *